US007982065B2

(12) United States Patent
Kimmich et al.

(10) Patent No.: US 7,982,065 B2
(45) Date of Patent: Jul. 19, 2011

(54) VINYL ESTER PRODUCTION FROM ACETYLENE AND CARBOXYLIC ACID UTILIZING HETEROGENEOUS CATALYST

(75) Inventors: Barbara F. M. Kimmich, Bernardsville, NJ (US); Hannah E. Toomey, Houston, TX (US); Qiang Yao, Baton Rouge, LA (US); G. Paull Torrence, League City, TX (US); Jan Cornelis van der Waal, Delft (NL); Bozena A. A. Silberova, Rotterdam (NL)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 12/387,749

(22) Filed: May 7, 2009

(65) Prior Publication Data

US 2010/0286441 A1 Nov. 11, 2010

(51) Int. Cl.
*C07C 69/76* (2006.01)
*C07C 67/04* (2006.01)

(52) U.S. Cl. .......................... 560/242; 560/103; 560/113

(58) Field of Classification Search .......................... None
See application file for complete search history.

(56) References Cited

U.S. PATENT DOCUMENTS

| | | | | |
|---|---|---|---|---|
| 2,066,075 A | 12/1936 | Reppe | | 260/106 |
| 2,339,066 A | 1/1944 | Fischer et al. | | 260/476 |
| 2,342,463 A | 2/1944 | Fischer et al. | | 260/476 |
| 2,472,086 A | 6/1949 | Beller et al. | | 260/468 |
| 3,062,836 A | 11/1962 | Martin | | 260/343.9 |
| 3,125,593 A | 3/1964 | Hargrave et al. | | 260/410.9 |
| 3,285,941 A | 11/1966 | Engel et al. | | 260/410.9 |
| 3,479,392 A | 11/1969 | Stern et al. | | 260/497 |
| 3,534,087 A * | 10/1970 | Leftin et al. | | 560/245 |
| 3,607,915 A | 9/1971 | Borsboom et al. | | 260/498 |
| 3,646,077 A | 2/1972 | Hübner et al. | | 260/410.9 N |
| 5,395,960 A * | 3/1995 | Heider et al. | | 560/242 |
| 5,430,179 A | 7/1995 | Lincoln et al. | | 560/261 |
| 6,500,979 B1 | 12/2002 | Wiese et al. | | 560/129 |
| 6,891,052 B1 | 5/2005 | Tanner et al. | | 554/161 |
| 2008/0308765 A1 * | 12/2008 | Staffel et al. | | 252/182.18 |

FOREIGN PATENT DOCUMENTS

| | | |
|---|---|---|
| CH | 324667 | 10/1957 |
| DE | 740678 | 11/1943 |
| DE | 1 161 878 | 1/1964 |
| DE | 1 237 557 | 3/1967 |
| DE | 10 2006 027 698 A1 | 12/2007 |

(Continued)

OTHER PUBLICATIONS

Transition-Metal-Catalyzed Addition of Heteroatom-Hydrogen Bonds to Alkynes, Alonso et al., Chem. Rev., 2004, 104 (6), 3079-3160 Atmospheric Vinylation of Several Haloacetic Acids and Benzoic Acid by Acetylene, Stanley R. Sandler, Journal of Chemical Engineering Data, vol. 18, No. 4, 1973, pp. 445-448.

(Continued)

*Primary Examiner* — Karl J Puttlitz
(74) *Attorney, Agent, or Firm* — Michael W. Ferrell

(57) ABSTRACT

A process for the selective production of vinyl ester by the reaction of a carboxylic acid with acetylene under heterogeneous catalytic conditions is disclosed and claimed. In a preferred embodiment of this invention, reaction of benzoic acid and acetylene in the presence of supported platinum catalyst at a temperature of from about 100 to 180° C. results in quantitative yields of vinyl benzoate.

16 Claims, 4 Drawing Sheets

FOREIGN PATENT DOCUMENTS

| | | |
|---|---|---|
| EP | 0 512 656 A2 | 11/1992 |
| EP | 512656 * | 11/1992 |
| EP | 0 622 352 A1 | 11/1994 |
| GB | 641438 | 8/1950 |
| GB | 1130245 | 10/1968 |
| WO | WO 2007/060176 | 5/2007 |

OTHER PUBLICATIONS

Vinylierung höherer Carbonsäuren an Katalysatorschmelzen, G. Hübner, Fette, Seifen, Anstrichmittel, 68, Jahrgang, Nr. 4, 1966, pp. 290-292; and Vinylierung, Walter Reppe and Mitarbeitern, Liebigs Ann. Chem. Bd. 601, Jul. 28, 1956, pp. 81-138.

* cited by examiner

VINYL ESTER PRODUCTION FROM ACETYLENE AND CARBOXYLIC ACID UTILIZING HETEROGENEOUS CATALYST

FIELD OF THE INVENTION

The present invention relates generally to a process for the production of vinyl ester from a carboxylic acid and acetylene. Specifically, the present invention relates to a series of heterogeneous catalyst systems that are suitable for the production of vinyl ester from a reaction of acetylene with a variety of carboxylic acids. In the preferred embodiments, the present invention relates to formation of vinyl benzoate (VB), vinyl 2-ethyl hexanoate (V2EH), and vinyl esters of various other neo carboxylic acids using heterogeneous catalysts.

BACKGROUND

There is a long felt need for an economically viable process for the formation of vinyl carboxylates such as, for example, vinyl benzoate. Vinyl carboxylates, such as for example vinyl benzoate, find use in a variety of applications including, for example, paints, adhesives and various other coating formulations as well as cement mortar admixtures.

It is known in the art that vinyl carboxylates can be formed from the reaction of a carboxylic acid with acetylene. A variety of catalysts have been proposed including base metals such as zinc, cadmium and mercury as well as precious metal catalysts such as rhenium, ruthenium, palladium, etc. In fact, the zinc carboxylate catalyzed process has been commercialized by Hexion Specialty Chemicals for the production of VEOVA™ Monomer 10, which is a vinyl ester of VERSATIC™ Acid 10, a synthetic saturated monocarboxylic acid of highly branched structure containing ten carbon atoms. More particularly, see U.S. Pat. No. 6,891,052 to Tanner et al., wherein is disclosed a zinc carboxylate catalyst, which is used for the formation of vinyl ester from the reaction of carboxylic acid with acetylene.

Similarly, various other processes have been reported in the literature wherein a carboxylic acid is reacted with acetylene to form the corresponding vinyl ester. See U.S. Pat. No. 3,607,915 to Borsboom et al. and Transition-Metal-Catalyzed Addition of Heteroatom-Hydrogen Bonds to Alkynes, Alonso et al., Chem. Rev., 2004, 104 (6), 3079-3160. In particular, Borsboom et al. disclose generally another method involving zinc-catalyzed carboxylic acid reaction with acetylene, as already noted above. Whereas, Alonso et al. provide an analysis of the state of the art for catalytic addition chemistry of the reaction of acetylene with a carboxylic acid. See also, U.S. Pat. No. 2,066,075 to Reppe, German Patent No. DE 740678 to I. G. Farbenindustrie A G, U.S. Pat. Nos. 2,339,066 and 2,342,463 to Fischer et al., British Patent No. GB 641,438A to General Aniline and Film Corporation, U.S. Pat. No. 2,472,086 to Beller et al., Swiss Patent No. CH 324667 to Staeger Reinhard, U.S. Pat. No. 3,062,863 to Fernholz et al., U.S. Pat. No. 3,125,593 to Hargrave et al., U.S. Pat. No. 3,285,941 to Engel et al., German Patent No. DE 1237557 to Shell Internationale Research, U.S. Pat. No. 3,646,077 to Hübner et al., and U.S. Pat. No. 6,500,979 to Wiese et al.

It has also been reported in the literature that a variety of Group VIII metal complex catalysts are effective in the formation of vinyl esters by the reaction of carboxylic acids with acetylene. See, for example, U.S. Pat. No. 3,479,392 to Stern et al. and U.S. Pat. No. 5,395,960 to Heider et al. Both Stern et al. and Heider et al. disclose vinylation of aromatic carboxylic acids in the presence of a catalyst based on ruthenium, rhodium, palladium, osmium, iridium, or platinum. Stern et al. is specifically drawn to a process for producing substituted olefins from a reactant other than acetylene or acetylenic compounds, and Heider et al. only disclose branched aliphatic carboxylic acids suitable for the catalyzed vinylation reaction, providing examples including 2-ethylhexanoic acid, 4-tert-butylbenzoic acid, suberic acid, and monomethyl succinate. However, Heider et al. disclose use of only ruthenium metal as a catalyst by way of examples and employ a very low molar ratio of carboxylic acid to ruthenium of about 25 to 100. That is, Heider et al. conditions require a large amount of catalyst per mole of vinyl ester produced. Additionally, Heider et al. employ longer reaction times of 7 to 17 hours rendering these conditions unsuitable for an industrial operation.

Palladium used as a co-catalyst with a cadmium or zinc catalyst is also known in the vinylation art. See, for example, German Patent No. DE 1161878 to Farbwerke Hoechst Aktiengesellschaft and British Patent No. GB 1,130,245 to Shell Internationale Research. Both patents disclose vinylation of benzoic acid and acetylene in the presence of a zinc or cadmium catalyst and a palladium co-catalyst. The palladium compounds taught are, however, free palladium metal or palladium chloride, and the processes are typically operated at temperatures above 120° C.

U.S. Pat. No. 5,430,179 to Lincoln et al. describes a homogeneous process for vinyl ester synthesis, such as vinyl benzoate, by ruthenium-catalyzed addition of carboxylic acids, including benzoic acid, to alkynes, including acetylene. Lincoln et al. disclose reaction conditions that include an optional solvent, such as toluene or mineral oil, and a temperature range of from about 40 to about 200° C. Lincoln et al. further disclose use of a ruthenium catalyst selected from a group that includes ruthenium dodecacarbonyl in concentrations ranging from about 50,000 ppm to about 0.5 ppm ruthenium based on the weight of the liquid phase reaction medium optionally in combination with a ligand such as triphenyl phosphine, tris(methoxyphenyl)-phosphine, or tris(p-fluoromethylphenyl)phosphine. However, Lincoln et al., disclose only one example of forming vinyl pivalate from the reaction of pivalic acid with acetylene under the reaction conditions disclosed therein.

WO 2007/060176 A1 to BASF Aktiengesellschaft provides a process for preparing vinyl carboxylates by reacting a carboxylic acid with an alkyne compound in the presence of a catalyst selected from a group of metal compounds including rhenium-based compounds. BASF specifically discloses reacting benzoic acid and acetylene in the presence of dirheniumdecacarbonyl; see Example 1. The Example teaches a molar ratio of carboxyl group to rhenium atom of 388, wherein the reaction takes place in a toluene solvent at 140° C. over a reaction time of 6 hours. The reported yield is 99%.

However, it has now been found that none of the existing processes is suitable for the production of vinyl benzoate (VB) or vinyl 2-ethyl hexanoate (V2EH) via the vinylation reaction, particularly, under heterogeneous catalytic conditions. Moreover, the conventional zinc catalysts provided unacceptable reaction rates and yields for an industrial scale-up operation. In addition, there are no heterogeneous catalytic processes that are readily employable for an industrial scale continuous, semi-continuous or batch operation for the production of vinyl esters such as VB or V2EH. Thus it is desirable to develop economically viable catalytically active reactions to form VB or V2EH from their respective carboxylic acids under mild reaction conditions involving heterogeneous supported metal catalysts.

SUMMARY OF THE INVENTION

It has now been unexpectedly found that vinyl benzoate can be made on an industrial scale from the reaction of a carboxylic acid, such as benzoic acid with acetylene with high selectivity and yield. More particularly, this invention provides a heterogeneous process for the selective formation of vinyl esters from their corresponding carboxylic acids and acetylene, which comprises reacting a carboxylic acid, optionally dissolved in a suitable organic solvent, with acetylene in the presence of a supported metal catalyst at a suitable reaction temperature and pressure, and optionally in the presence of one or more ligands or additives or a mixture thereof.

The catalyst employed in the process of this invention is a supported metal catalyst. Examples of supported metals that are suitable in the process of this invention include without any limitation iridium, palladium, platinum, rhenium, rhodium and ruthenium.

Any of the known catalyst supports can be employed to support the metals of the process of this invention. Representative catalyst supports include without any limitation, carbon, graphite, silica, titania, alumina, calcium silicate, calcium carbonate, silica-alumina, silica aluminate, zirconia, barium carbonate, barium sulfate, and the like.

It has now been found that use of certain ligands and additives enhance the catalytic activity of certain catalysts of this invention, which aspect is described in detail hereinbelow. However, it should also be noted that other combinations of certain catalysts of this invention in the presence of certain ligands and additives exhibit diminished activity, which again becomes apparent from the detailed description that follows. Various ligands and additives that can bring about the vinylation reaction with a carboxylic acid and acetylene can be employed in the process of this invention.

It has also been found that by suitable selection of the catalyst and optionally the ligand(s) and additive(s) and utilizing them in suitable amounts results in at least 50 percent (%) conversion of a carboxylic acid and the selectivity to vinyl ester can be at least 50 percent (%). In addition, by suitable practice of this invention it is possible to attain a Relative Activity of at least 80 and up to about 2000.

Other aspects and advantages of the present invention are described in the detailed description below and in the claims.

BRIEF DESCRIPTION OF THE DRAWINGS

The invention is described in detail below with reference to the appended drawings, wherein like numerals designate similar parts. In the Figures.

DETAILED DESCRIPTION OF THE INVENTION

Figure 1:
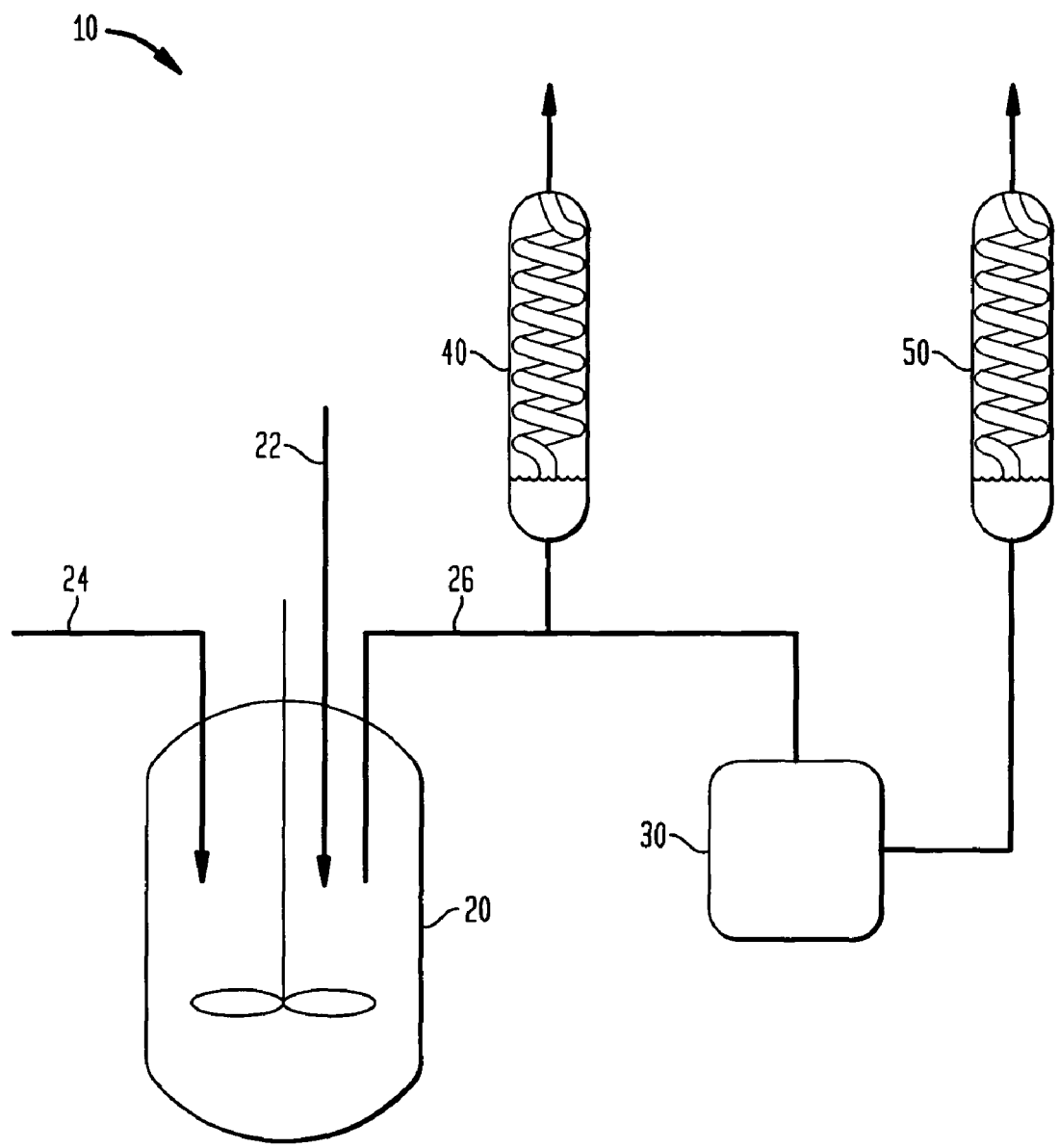
FIG. 1 is a schematic diagram of an apparatus suitable for producing vinyl ester from a carboxylic acid and acetylene in accordance with the process of the present invention.

The invention is described in detail below with reference to several embodiments and numerous examples. Such discussion is for purposes of illustration only. Modifications to particular examples within the spirit and scope of the present invention, set forth in the appended claims, will be readily apparent to one of skill in the art. Terminology used herein is given its ordinary meaning consistent with the exemplary definitions set forth immediately below.

As used herein, a heterogeneous catalyst refers to a catalyst that is in a different phase than the reactants during catalysis. In order for the reaction to occur, one or more of the reactants must diffuse to the catalyst surface and adsorb onto it. After reaction, the products must desorb and diffuse away from the surface. In contrast, as used herein a homogeneous catalyst refers to a catalyst that is present in the same phase as the reactants.

Mole percent (mole %) and like terms refer to mole percent unless otherwise indicated. Weight percent (wt % or %) and like terms refer to weight percent unless otherwise indicated.

"Conversion" refers to the fraction of reactant consumed in the reaction and is expressed as a mass percentage based on the amount of carboxylic acid in the feed. The conversion of carboxylic acid (CA) is calculated from gas chromatography (GC) data using the following equation:

$$CA \text{ conversion}(\%) = 100 * \frac{\text{mass } CA, \text{in} - \text{mass } CA, \text{out } (GC)}{\text{mass } CA, \text{in}}$$

where mass CA, in=mass of carboxylic acid loaded (weighed in) into the reactor, and mass CA, out (GC)=mass of carboxylic acid after the reaction based on GC data.

"Selectivity" refers to the amount of vinyl ester produced relative to the carboxylic acid consumed and is expressed as a mole percent based on converted carboxylic acid. For example, if the conversion is 50 mole % and 50 mole % of the converted carboxylic acid is converted to vinyl ester, we refer to the vinyl ester selectivity as 50%. Selectivity to vinyl ester (VE) is calculated from gas chromatography (GC) data using the following equation:

$$\text{Selectivity to } VE(\%) = 100 * \frac{\text{mol } VE, \text{out } (GC)}{\text{mol } CA, \text{in} - \text{mol } CA, \text{out } (GC)}$$

"Yield" refers to the amount of vinyl ester produced relative to the carboxylic acid loaded into the reactor and is expressed as a mole percent based on carboxylic acid loaded into the reactor. Yield of vinyl ester (VE) is calculated from gas chromatography (GC) data using the following equation:

$$\text{Yield of } VE(\%) = 100 * \frac{\text{mol } VE, \text{out } (GC)}{\text{mol } CA, \text{in } (GC)}$$

where mol CA, in=number of moles of carboxylic acid loaded (weighed in) into the reactor, mol CA, out (GC)=number of moles of carboxylic acid after the reaction based on GC data, and mol VE, out (GC)=number of moles of vinyl ester after the reaction based on GC data.

The catalyst activity is determined by Turnover Number (TON) using the following equation. TON refers to the average amount of desired product produced by each metal atom contained in the catalyst.

$$TON = \frac{\text{mol } VE, \text{ out } (GC)}{\text{mol } Cat * N \text{ Metal atoms}}$$

where mol Cat=number of moles of catalysts loaded (weighed in) into the reactor, and N Metal atoms=moles of metal atoms in one mole of catalyst.

For example, a Turnover Number calculated for platinum at a 5 wt % loading on carbon used in the production of vinyl benzoate is determined by computing as the numerator: the grams of vinyl benzoate per run divided by the molecular weight of vinyl benzoate, 148.15 gm/mol; and computing as the denominator: the loading value, 0.05 times 1 gram of platinum, divided by the molecular weight of platinum, 195.084 gm/mol.

For Turnover Numbers determined under the following conditions, the Turnover Number is referred to herein as Relative Activity. The conditions for determining Relative Activity of the catalyst or system include a batch run duration of 4 hours, a charged molar ratio of carboxylic acid to catalyst metal of about 385:1, and a temperature of 120° C. When a ligand is used, the ligand is available in a molar ratio of ligand to catalyst metal of 1:1.

The reaction proceeds in accordance with the following chemical equation:

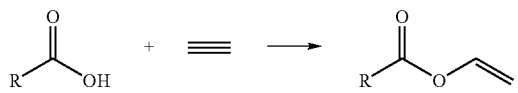

where R is an alkyl group, including a primary, a secondary or a tertiary alkyl group; a cycloalkyl group; or an aryl group such as phenyl. Thus, when R is phenyl, the acid employed is benzoic acid (BA) and the product formed is vinyl benzoate (VB) in accordance with the following chemical equation.

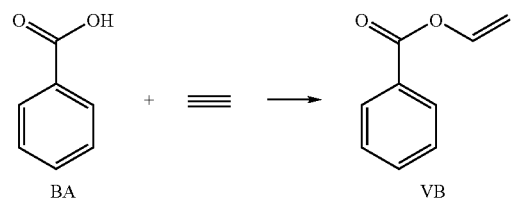

Similarly, when R is 2-ethylpentyl, the acid employed is 2-ethylhexanoic acid (2EHA) and the product formed is vinyl 2-ethylhexanoate (V2EH) in accordance with the following chemical equation.

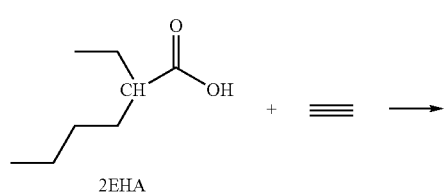

-continued

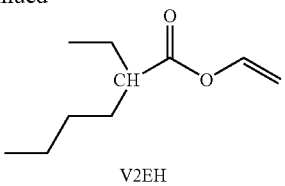

It has now been unexpectedly found that a vinyl ester can be made on an industrial scale from the reaction of a corresponding carboxylic acid with acetylene with high selectivity and yield. More particularly, this invention provides a heterogeneous process for the selective formation of a vinyl ester from its corresponding carboxylic acid and acetylene, which comprises reacting a carboxylic acid optionally dissolved in a suitable organic solvent with acetylene in the presence of a supported metal catalyst at a suitable reaction temperature and pressure, and optionally in the presence of one or more ligands or additives or a mixture thereof. Such solvents may include, for example, acetonitrile, butyl benzoate, diethyleneglycoldibutylether, mesitylene, mineral oil, and toluene.

Various carboxylic acids known in the art can be employed in the process of this invention to form corresponding vinyl esters. Illustrative of suitable carboxylic acids for the practice of the invention are aliphatic or aromatic monocarboxylic, dicarboxylic and polycarboxylic acids. Examples of aliphatic monocarboxylic acids include the following: acetic acid, propionic acid, butyric acid, valeric acid, hexanoic acid, heptanoic acid, octanoic acid, nonanoic acid, decanoic acid, 2-methylpropionic acid, 2-methylbutyric acid, 3-methylbutyric acid, 2-methylpentanoic acid, 2-ethylhexanoic acid, 2-propyl heptanoic acid; pivalic acid and other neo acids such as neodecanoic acid, neotridecanoic acid and neononanoic acid; stearic acid, and fatty acids. Examples of aromatic mono- and di-carboxylic acids include the following: benzoic acid, terephthalic acid, isophthalic acid and phthalic acid. Other aromatic carboxylic acids include substituted benzoic acid, such as for example, o-, m-, or p-toluic acid, o-, m-, or p-chlorobenzoic acid, and the like. Examples of aliphatic di- and polycarboxylic acids include: adipic acid, succinic acid, malic acid, maleic acid and polyacrylic acids. Various other carboxylic acids that are suitable in the process of this invention include crotonic acid, acrylic acid, methacrylic acid, salicylic acid, cinnamic acid, and cyclohexanoic acid.

Preferably, the acids that can be employed in the process of this invention include benzoic acid and various branched aliphatic carboxylic acids, such as for example 2-ethylhexanoic acid, 2-methylhexanoic acid, 2-ethylheptanoic acid, and the like.

Another particular class of carboxylic acids that are suitable in this invention is the neo acids. Neo acids are highly branched aliphatic carboxylic acids. In general, neo acids are trialkyl acetic acids, which include a tetra substituted alpha-carbon. Alkyl groups on the substituted alpha-carbon create a steric effect, i.e. hinder the ability of the neo acid to react. Methyl substituted alpha-carbon neo acids are the least hindered of the neo-acids. The reactivity of the neo acid primarily depends on the molecular weight and structure of the neo acid. In general, the greater the molecular weight of the alkyl groups on the alpha-carbon, the greater the steric effect and the less reactive the neo acid. The neo acids that are suitable in this invention may be expressed according to formula I:

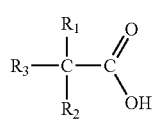

Formula I where each of $R_1$, $R_2$ and $R_3$ is an alkyl group having from 1 to 10 carbons and the total carbons in $R_1+R_2+R_3$ is from 3 to 30. Examples of neo acids include without any limitation neopentanoic acid, neoheptanoic acid, neodecanoic acid, etc.

Several of the neo acids are commercially available, for example from ExxonMobil Chemical Company. Specific examples of commercially available neo acids include the ones listed above and proprietary neo acids such as neo 910 and neo 913 from ExxonMobil Chemical Company.

Although the process of this invention is intended to make vinyl ester from the reaction of acetylene with a carboxylic acid, various other known primary alkynes that can bring about such a vinylation reaction can also be employed in the process of this invention. Generally, unsubstituted alkynes and mono-substituted alkynes that do not interfere with the addition reaction of the process of this invention may be used. Representative substituents include alkyl, alkoxy, aryl, aryloxy, acetoxy, carboxyl and halo groups. Alkynes typically have from 2 to 10 carbon atoms and suitable alkynes include substituted or unsubstituted primary alkynes such as acetylene, methyl acetylene, phenyl acetylene, 1-butyne, 1-pentyne, 1-hexyne, 1-heptyne, 1-octyne, 1-nonyne, 1-decyne, and the like. More suitable alkynes useful in the practice of the invention include acetylene and methyl acetylene.

The catalyst employed in the process of this invention is a supported metal catalyst. Examples of supported metals that are suitable in this process of the invention include without any limitation iridium, palladium, platinum, rhenium, rhodium and ruthenium.

Any of the known catalyst supports can be employed to support the metals of the process of this invention. Representative catalyst supports include without any limitation, carbon, activated carbon, graphite, silica, titania, alumina, calcium silicate, calcium carbonate, silica-alumina, silica aluminate, zirconia, barium carbonate, barium sulfate, and the like.

The process according to the invention may be practiced using any conventional reactor known in the art, under batch, semi-batch, or continuous conditions. The reactor may employ a fixed bed, a fluidized bed, or a moving bed. For example, a continuous stirred-tank reactor (CSTR) with acetylene sparging system, mild mechanical agitation and candle filter filtration (to hold the catalyst particles inside the reactor) can be a commercial option. Alternatively a trickle-bed, where the carboxylic acid and the acetylene are introduced co-currently from the top may be used. Another fixed bed reactor type is the bubble column where acetylene comes in from the bottom, catalyst is deposited inside the reactor tower and liquid carboxylic acid is introduced from the top. These examples are not meant to be limiting. A modern reactive distillation system where each tray is coated with catalyst can also be used, for instance.

One of skill in the art would likely select a reactor size necessary to optimize reactor throughput by whatever variable is appropriate, for instance reactor productivity (STY) or conversion. The size and shape of heterogeneous catalyst particles selected are dependent upon the type of reactor used. Thus, the catalyst may be in the form of pellets, powder, saddles, spheres, etc.

In accordance with the invention, reaction of a carboxylic acid with acetylene can be carried out in a variety of configurations such as those discussed above, including a batch reactor involving a single reaction zone and a continuous reactor wherein the reactant feed is passed through a fixed bed or a fluidized catalyst bed. The process of this invention can also be carried out using any of the other known techniques in the art such as a semi-continuous process using a stirred tank reactor, etc. For example, in a single reaction zone the catalyst may be a layered fixed bed, if so desired. An adiabatic reactor could be used, or a shell and tube reactor provided with a heat transfer medium could be used. The fixed bed can comprise a mixture of different catalyst particles which include multiple catalysts, ligands and additives as further described herein. The fixed bed may also include a layer of particulate material making up a mixing zone for the reactants. A reaction mixture including a solution of carboxylic acid, if so desired, acetylene and optionally an inert carrier gas is fed to the bed as a stream under pressure to the mixing zone. Alternatively, a carboxylic acid itself can be fed with acetylene optionally with an inert carrier gas, such as nitrogen. The stream is subsequently supplied (by way of pressure drop) to the reaction zone or layer. The reaction zone comprises a catalytic composition including a suitable supported metal catalyst where a carboxylic acid such as benzoic acid is reacted with acetylene. Any suitable particle size may be used depending upon the type of reactor, throughput requirements and so forth.

Although various metal loading levels on the supported catalysts known to one skilled in the art can be employed in the process of this invention it is preferred that a supported metal catalyst employed contains about 0.1 weight percent to about 20 weight percent of metal on a suitable catalyst support. As described further below it may also be advantageous that the supported metal catalysts that are suitable in the process of this invention may optionally contain a ligand and/or other additives including a second and/or a third supported metal on the same catalyst support. The following metals may be mentioned as those metals suitable as a second and/or third metal without any limitation: palladium, cadmium, zinc and a mixture thereof. Typically, it is preferred that only the supported metal catalyst as described herein may be used in the process of this invention. However, other ligands and/or additives may be added to the reaction feed as additional catalytic enhancers or promoters.

As noted above, various catalyst supports known in the art can be used to support the catalysts of this invention. Preferred supports are carbon, activated carbon, graphite, calcium carbonate, titania, alumina, alumina-silica, and barium sulfate. More preferably, carbon, activated carbon, alumina, titania or zirconia are used as supports. It should be noted that various supported metal catalysts which are suitable in this invention are commercially available and may be used with or without catalyst activation.

In an embodiment of this invention the preferred catalyst support is carbon. Various forms of carbon known in the art that are suitable as catalyst support can be used in the process of this invention. Carbon supports that are suitable in this invention include non-activated as well as activated forms. Activation of carbon support can be performed using any of the methods known in the art. See for example, U.S. Pat. No. 5,064,801, wherein a process for activating a certain carbon catalyst is disclosed. Another type of carbon support is a graphitized carbon, particularly the high surface area graphitized carbon as described in Great Britain U.S. Pat. No. 2,136,704. The carbon is preferably in particulate form, for example, as pellets. The size of the carbon particles will depend on the pressure drop acceptable in any given reactor (which gives a minimum pellet size) and reactant diffusion constraint within the pellet (which gives a maximum pellet size).

The carbon catalyst supports that are suitable in the process of this invention preferably are porous carbon catalyst supports. With the preferred particle sizes the carbon will need to be porous to meet the preferred surface area characteristics.

The catalyst supports including the carbon catalyst supports may be characterized by their BET, basal plane, and edge surface areas. The BET surface area is the surface area determined by nitrogen adsorption using the method of Brunauer Emmett and Teller J. Am. Chem. Soc. 60,309 (1938). The basal plane surface area is the surface area determined from the heat of adsorption on the carbon of n-dotriacontane from n-heptane by the method described in Proc. Roy. Soc. A314 pages 473-498, with particular reference to page 489. The edge surface area is the surface area determined from the heat of adsorption on the carbon of n-butanol from n-heptane as disclosed in the Proc. Roy. Soc. article mentioned above with particular reference to page 495.

The preferred carbon catalyst supports for use in the present invention have a BET surface area of at least 100 $m^2/g$, more preferably at least 200 $m^2/g$, most preferably at least 300 $m^2/g$. The BET surface area is preferably not greater than 1000 $m^2/g$, more preferably not greater than 750 $m^2/g$.

The preferred carbon support may be prepared by heat treating a carbon-containing starting material. The starting material may be an oleophilic graphite, e.g. prepared as disclosed in Great Britain U.S. Pat. No. 1,168,785, or may be a carbon black.

As noted above, the loading levels of metal on the catalyst support is generally in the range of about 0.1 weight percent to about 20 weight percent. As already noted above, the amount of a second or third component loaded on a support is not very critical in this invention and can vary in the range of about 0.1 weight percent to about 10 weight percent. Preferably, the supported metal catalyst of this invention is free of any other loading. A metal loading of about 0.3 weight percent to about 6 weight percent based on the weight of the support is particularly preferred. Thus, for example, 0.5 to 10 weight percent of platinum supported on carbon, activated carbon, graphite, alumina, zirconia or titania is particularly a preferred catalyst. More preferably, the platinum loading level is from about 0.5 weight percent to about 5 weight percent. Other supports suitable for supporting platinum metal include without any limitation the following: barium sulfate, calcium carbonate and silica.

Similarly, a catalyst containing about 1 to 3 weight percent of rhenium supported on carbon is also a preferred catalyst. Other suitable catalysts include a catalyst containing about 1 to 6 weight percent of rhodium supported on carbon, a catalyst containing about 1 to 3 weight percent of ruthenium supported on silica, a catalyst containing about 1 to 6 weight percent of palladium supported on carbon, a catalyst containing about 1 to 6 weight percent of palladium supported on carbon, which may also contain about 1 to 4 weight percent of platinum as a second metal, a catalyst containing about 1 to 6 weight percent of iridium supported on carbon, a catalyst containing about 1 to 6 weight percent of iridium supported on calcium carbonate and iridium (IV) oxide itself as a supported metal catalyst.

As already noted above, many of the supported metal catalysts useful in this invention are commercially available. However, the supported metal catalysts can also be readily prepared using any of the methods known in the art, such as for example by metal impregnation techniques. The metal impregnation can be carried out using any of the known methods in the art. Typically, before impregnation the supports are dried at 120° C. and shaped to particles having size distribution in the range of about 0.2 to 0.4 mm. Optionally, the supports may be pressed, crushed and sieved to a desired size distribution. Any of the known methods to shape the support materials into desired size distribution can be employed.

For supports having low surface area, such as for example alpha-alumina, the metal solutions are added in excess until complete wetness or excess liquid impregnation so as to obtain desirable metal loadings.

As noted above, the supported metal catalysts used in the process of this invention may be bimetallic catalysts. The bimetallic catalysts are generally impregnated in two steps. First, the second metal is added, followed by the "main" metal. Each impregnation step is followed by drying and calcination. The bimetallic catalysts may also be prepared by co-impregnation. In the case of trimetallic containing catalysts, a sequential impregnation may be used, starting with the addition of the secondary or tertiary metal. The second impregnation step may involve co-impregnation of the two principal metals. For example, Pd/Pt on carbon may be prepared by a first impregnation of platinum nitrate, followed by the impregnation of palladium acetate. Again, each impregnation is followed by drying and calcination. In most cases, the impregnation may be carried out using metal nitrate solutions. However, various other soluble salts which upon calcination release metal ions can also be used. Examples of other suitable metal salts for impregnation include metal hydroxide, metal oxide, metal acetate, ammonium metal oxide, such as ammonium heptamolybdate hexahydrate, metal acids, such as perrhenic acid solution, metal oxalate, and the like.

It has now been found that the use of certain ligands and additives enhance the catalytic activity of the supported metal catalysts of this invention. Various ligands and additives that can bring about the vinylation reaction with a carboxylic acid and acetylene can be employed in the process of this invention. Examples of ligands include without any limitation the following: triphenylphosphine, 1,2-diphenylphosphinobenzene (1,2-DPPB), o-bipyridyl, (±)-2,2'-bis(diphenyl-phosphino)-1,1'-binaphthalene, 1,1'-bis(diphenylphosphino)ferrocene, 4,5-bis(diphenylphosphino)-9,9-dimethylxanthene, diphenyl-2-pyridylphosphine, oxydi-2,1-phenylenebis (diphenylphosphine), tris(p-trifluoromethylphenyl)-phosphine [$P(p-CF_3C_6H_4)_3$], tris(1-naphthyl)phosphine, tris(2,4,6-trimethoxyphenyl)phosphine and tris(4-methoxyphenyl) phosphine.

Examples of additives include aluminum acetylacetonate, aluminum chloride, cadmium acetylacetonate, cerium chloride, iron chloride, potassium acetate, lithium acetate, lithium bromide, lithium chloride, sodium benzoate, sodium phosphate, sodium tetrafluoroborate, sodium chloride, sodium iodide, sodium trifluoroacetate, potassium acetate, para-benzoquinone, palladium acetate, palladium acetylacetonate, palladium chloride, vinyl acetate, triruthenium-do-decacarbonyl ($Ru_3(CO)_{12}$), zinc bromide, zinc chloride, benzoic anhydride, tri-(n-butyl)amine or tributylamine, tetra-(n-butyl)ammonium chloride, tetrabutyl-ammonium acetate, sodium phosphate and tetrabutylammonium acetate.

In an aspect of this invention the process of this invention is generally carried out in a batch operation using a stirred tank reactor. The supported metal catalyst is slurried in a suitable solvent. To this slurry is added a solution of carboxylic acid and any desirable ligands and/or additives. The reactor is heated to desirable temperatures under an inert atmosphere, such as nitrogen, and acetylene is fed into the reactor for a certain length of time. Typically, as already discussed above, the reaction times may vary depending upon the catalyst and can range from about 1 hour to 4 hours.

In another aspect of this invention the reaction can also be carried out in a continuous process. In this aspect, the reactants, such as benzoic acid, suitably as a solution, and acetylene, are fed into a reactor packed with the supported metal catalyst. As noted, the carboxylic acid can be fed into the reactor as a solution dissolved in a suitable solvent or neat if it is in the liquid form, such as for example 2-ethylhexanoic acid. Inert gas such as nitrogen may be used as a carrier gas to feed both the carboxylic acid and acetylene at a desirable reaction temperature as discussed herein.

Contact or residence time can also vary widely, depending upon such variables as amount of carboxylic acid and acetylene, amount and type of catalyst and reactor, temperature and pressure employed. Typical contact times range from a fraction of a second to more than several hours when a catalyst system other than a fixed bed is used, with preferred contact times, at least for vapor phase reactions, between about 0.5 and 100 seconds.

Typically, in this aspect of the invention, the catalyst employed is in a fixed bed reactor, e.g. in the shape of an elongated pipe or tube, where the reactants, typically in vapor form or as a solution, are passed over or through the catalyst. Other reactors, such as fluid or ebullient bed reactors, can be employed, if desired. In some instances, it is advantageous to use the supported metal catalysts in conjunction with an inert material to regulate the pressure drop, flow, heat balance or other process parameters in the catalyst bed including the contact time of the reactant compounds with the catalyst particles.

As apparent from the Examples that follow, by practice of this invention it is possible to obtain high conversion and selectivity to vinyl esters. That is, by suitable selection of the catalyst and optionally the ligand(s) and additive(s) it has now been found that high conversion of carboxylic acid to vinyl ester, for example benzoic acid to vinyl benzoate, can be achieved. More particularly, it has been observed that utilization of a desirable amount of catalyst in combination with optional ligand(s) and additive(s) results in at least 50 percent (%) conversion of carboxylic acid. Additionally, the selectivity to vinyl ester is found to be at least 50 percent (%). Furthermore, by suitable practice of this invention it is possible to attain a Relative Activity of at least 80 and up to about 2000.

The process of this reaction can be carried out using any reaction temperature such that the intended reaction of a carboxylic acid with acetylene to form a vinyl ester can take place resulting in high selectivity to vinyl ester and at high conversions of carboxylic acid. Typically, such reactions in a batch operation are carried out at a temperature range from about 100° C. to about 180° C. For example, the reaction temperature can range from about 110° C. to about 170° C. under certain catalytic conditions. The reaction temperature can also range from about 120° C. to about 160° C. under certain other catalytic conditions. In some cases the reaction temperature ranges from about 130° C. to about 150° C. In certain other situations the reaction temperature ranges from about 135° C. to about 145° C. However, in a continuous operation such as the one described above even higher reaction temperatures may be employed.

The reaction can also be carried out at any pressure condition so as to selectively form vinyl ester from carboxylic acid at high conversions, such as for example sub-atmospheric, atmospheric or super-atmospheric conditions. Generally, it is preferred that the reaction is carried out at a pressure in the range of from about one atmosphere to two atmospheres absolute. More particularly, the reaction is carried out at atmospheric pressure conditions in an inert atmosphere, such as for example in an atmosphere of nitrogen, helium or argon.

In general, the amount of acetylenic compound employed is equimolar or slightly in excess of equimolar to the carboxylic group to be converted. Thus, when the carboxylic acid used is a mono-carboxylic acid, a molar ratio of acetylene to acid is generally from about 1:1 to 100:1, preferably from about 1.2:1 to 30:1, and more preferably from about 1.5:1 to about 10:1. Accordingly, acetylenic compound is proportionately used in higher quantities when dibasic and/or other polybasic acids are employed.

In an aspect of this invention, the process of this invention can be carried out with a small amount of the catalyst. That is, large amounts of carboxylic acids such as benzoic acid (BA) can be converted to a vinyl ester such as vinyl benzoate (VB) in the presence of small amounts of catalyst material. Generally, the reaction mixture comprises a mixture of desired supported metal catalyst and carboxylic acid in a molar carboxylic acid (CA) to metal ratio of from about 4000:1 to about 100:1. More typically, the molar CA/metal ratio is about 1000:1. However any other molar CA/metal ratio that would bring about the desired conversion and selectivity to vinyl ester such as VB can be employed in the process of this invention.

In another aspect of this invention, the catalyst exhibits a very high Relative Activity (moles of vinyl ester/metal atom) in the process of this invention. Typically, the Relative Activities range from about 80 to about 2000, preferably Relative Activities range from about 100 to about 1500, more preferably from about 100 to about 1000.

In a further aspect of this invention, very high selectivity to vinyl ester, such as for example vinyl benzoate, can be obtained by suitable practice of the process of this invention. Typically, the selectivity to vinyl ester based on carboxylic acid consumed can at least be 60 percent. More specifically, the selectivity to vinyl ester based on carboxylic acid consumed may be at least 80 percent. Even more specifically, the selectivity to vinyl ester based on carboxylic acid consumed is at least 99 percent.

As already discussed above, depending upon the configuration of the supported metal catalyst system and the type of reactor, the process of this invention can be carried out to a desirable length of time in order to obtain the best catalyst activity, Relative Activities and selectivity to vinyl ester, such as VB or V2EH. Typically, the reactions are run in a batch mode for a period ranging from about 1 hour to about 5 hours. More typically, the reaction is carried out in the batch mode for a period of about four hours. However, the process of this invention can be carried out in a semi-continuous or continuous manner using any of the known process techniques in the art.

Thus in one embodiment of this invention, there is provided a supported metal catalyst wherein the metal is platinum and the catalyst support is carbon, activated carbon, graphite, titania, alumina, zirconia, alumina-silica, barium sulfate and calcium carbonate. In this aspect of the invention, the loading of platinum is from about 0.5 weight percent to about 10 weight percent, preferably from about 0.5 weight percent to about 6 weight percent. In this aspect of the invention it has now been found that the use of certain ligands as described herein may enhance the catalytic activity of the platinum as observed by increase in either selectivity to vinyl ester, such as VB or conversion of carboxylic acid, such as BA or both. It has been observed that ligands such as 1,2-DPPB or triphenylphosphine generally exhibit positive or negative effects on the catalytic activity of platinum depending upon the temperature of the reaction as further discussed below. Similarly, it has also been observed that addition of certain additives may also have positive effect on supported platinum catalysts. Examples of such additives include sodium benzoate, benzoic anhydride, tetrabutylammonium acetate, tributylamine, and the like. In general, the additives increase the rate of conversion of carboxylic acid, such as BA.

In general, it has now been found that alumina, carbon, activated carbon, zirconia and titania are the preferred catalyst supports for platinum. The following supported platinum catalysts are particularly preferred:

0.5% platinum supported on carbon;
1% platinum supported on carbon;
3% platinum supported on activated carbon;
5% platinum supported on activated carbon;
0.5% platinum supported on alumina;
5% platinum supported on alumina;
0.9% platinum supported on zirconia; and
5% platinum supported on titania.

All of the above listed supported platinum catalysts are commercially available and/or can be prepared in accordance with any of the literature procedures known to one, skilled in the art.

Typically, the activity of the supported platinum metal catalyst increases with increasing temperature from about 120° C. to about 170° C. The Relative Activities typically increase with increasing temperature and maximum Relative Activities are typically observed at around 160° C. under batch mode operation. However, even higher Relative Activities may be observed in a continuous operation using a fixed bed reactor at even higher temperatures. As already noted above, use of certain ligands may have a positive or negative effect on the conversion or the selectivity especially at varied reaction temperatures. It has now been observed that the use of ligands such as triphenylphosphine or 1,2-DPPB exhibit different effects on the supported platinum catalyst with varied reaction temperatures. Although both ligands generally lowered activities for supported platinum metal catalysts, Relative Activity and conversion values increase with increasing temperature in the presence of triphenylphosphine, whereas the values are evenly suppressed across temperatures in the presence of 1,2-DPPB.

For most supported platinum catalysts, increasing temperature generally results in an increase in the conversion of carboxylic acid, such as benzoic acid, and a decrease in the selectivity to vinyl ester, such as vinyl benzoate. However, as noted above, the temperature of about 160° C. is preferred to obtain optimal conversion and selectivity to vinyl benzoate in a batch mode.

Typically, the reaction time used in supported platinum catalysts is from about one hour to about four hours. Preferably, the reaction time is about two to about four hours.

In general, the Relative Activities increase with higher molar carboxylic acid (CA)/metal ratio. For example, the molar CA/metal ratio can range from about 300 to 4000, more preferably from about 380 to about 3000, and even more preferably from about 1200 to about 2500. Relative Activities of up to 600 or higher can be achieved with 0.5% platinum supported on alumina, 0.9% platinum supported on zirconia, or 0.5% to 1% platinum supported on carbon. More particularly, it has now been observed that at a molar BA to platinum atom ratio of about 1450, Relative Activities of about 700 can be achieved and at a molar BA to platinum atom ratio of about 2300, Relative Activities of about 700 to 800 can be achieved.

Generally, the type of catalyst support employed has an effect on the conversion and selectivity to vinyl ester. It has now been observed that carbon, zirconia or titania exhibit higher Relative Activities. Titania exhibits highest conversion whereas carbon exhibits highest selectivity.

In general, the supported platinum catalysts are dried in nitrogen atmosphere at 100° C. for 16 hours before use. The tested catalysts may be reused after drying again at 100° C. for 16 hours. The catalysts may also be dried at a temperature range of 50° C. to 100° C. in air for a sufficient length of time, such as for example about 16 hours. However, it is preferred that the supported platinum catalysts are dried in an inert atmosphere such as nitrogen.

In another embodiment of this invention, there is further provided a supported metal catalyst wherein the metal is rhenium and the catalyst support is carbon. In this aspect of the invention, the loading of rhenium is from one (1) weight percent to about six (6) weight percent, preferably the loading of rhenium is from about two (2) weight percent to about four (4) weight percent. Again in this aspect of the invention, certain of the ligands and/or additives can be used in combination with a supported rhenium catalyst. A specific example of a supported rhenium catalyst is two (2) weight percent rhenium on carbon, which is commercially available.

In another embodiment of this invention, there is further provided a supported metal catalyst wherein the metal is rhodium and the catalyst support is carbon. In this aspect of the invention, the loading of rhodium is from one (1) weight percent to about ten (10) weight percent, preferably from about two (2) weight percent to about six (6) weight percent. Again in this aspect of the invention, certain ligands and/or additives can be used in combination with a supported rhodium catalyst. A specific example of a supported rhodium catalyst is five (5) weight percent rhodium on carbon, which is commercially available.

It has now been observed that use of triphenylphosphine with 5 weight percent rhodium on carbon has a positive effect on the conversion and selectivity to vinyl esters such as VB.

In another embodiment of this invention, there is further provided a supported metal catalyst wherein the metal is ruthenium and the catalyst support is silica. In this aspect of the invention, the loading of ruthenium is from one (1) weight percent to about ten (10) weight percent, preferably from about two (2) weight percent to about six (6) weight percent. Again in this aspect of the invention, certain ligands and/or additives can be used in combination with a supported ruthenium catalyst. A specific example of a supported ruthenium catalyst is 1.85 weight percent ruthenium on silica, which is commercially available.

It has now been observed that use of a ligand such as triphenylphosphine has a positive effect on the activity of the ruthenium supported on silica. The reaction temperature that can be employed with a supported ruthenium catalyst is generally from about 150° C. to about 170° C. in a batch operation for the conversion of carboxylic acid to vinyl ester, such as BA to VB. Any of the solvents as described herein can be employed with ruthenium catalysts, if so desired. An example of a suitable solvent is butyl benzoate.

In another embodiment of this invention, there is further provided a supported metal catalyst wherein the metal is palladium and the catalyst support is carbon. This catalyst further contains a second metal which is platinum. In this aspect of the invention, the loading of palladium is from one (1) weight percent to about ten (10) weight percent, preferably from about two (2) weight percent to about six (6) weight percent. Again in this aspect of the invention, certain ligands and/or additives can be used in combination with a supported palladium catalyst. A specific example of a supported palladium catalyst is three (3) weight percent palladium on carbon, which further contains platinum. This catalyst is commercially available.

The reaction temperature that can be employed with a supported palladium catalyst is generally from about 150° C. to about 170° C. in a batch operation for the conversion of carboxylic acid to vinyl ester, such as for example BA to VB. Again, any of the solvents as described herein can be employed with palladium catalysts, if so desired. An example of a suitable solvent is butyl benzoate.

In another embodiment of this invention, there is further provided a supported metal catalyst wherein the metal is iridium and the catalyst support is either carbon or calcium carbonate. In this aspect of the invention, the loading of iridium is from one (1) weight percent to about ten (10) weight percent, preferably from about two (2) weight percent to about six (6) weight percent. Again in this aspect of the invention, certain ligands and/or additives can be used in combination with a supported iridium catalyst. Specific examples of supported iridium catalysts are: five (5) weight percent iridium on carbon or five (5) weight percent iridium on calcium carbonate, both of which are commercially available. In addition, iridium(IV) oxide can be used as such in the process of this invention as a heterogeneous supported iridium metal catalyst.

FIG. 1 illustrates a laboratory scale system 10 for the production of vinyl esters by the reaction of a carboxylic acid and acetylene using the catalyst system of this invention. The system 10 of FIG. 1 comprises a stirred reactor 20 and a collector 30. The reactor 20 and the collector 30 are each provided with a condenser 40, 50 for which a conventional means of pressure regulation is provided, such as a bubbler, not shown. Briefly, a suitable reactor 20 of desired size, such as a 250 mL three-neck glass flask, is employed. The reactor 20 is initially charged with a desired carboxylic acid, suitable solvent and predetermined amounts of catalyst, and if necessary, ligands and additives. Then the reactor 20 is purged with nitrogen and heated to desired reaction temperature. Acetylene is then bubbled into the reaction mixture at a desired rate via line 24 and additional carboxylic acid may be charged, with solvent as necessary, via line 22. As the reaction proceeds, the vinyl ester product is removed via line 26 and is fractionated and collected in a collection flask 30. The condensers 40, 50 serve to recover an optimal amount of product and solvent while releasing non-condensible gases. The temperature of the condensers 40, 50 is regulated by conventional means known to one of skill in the art. The order of addition of the reactants is not crucial in the process of this invention.

Figure 2:
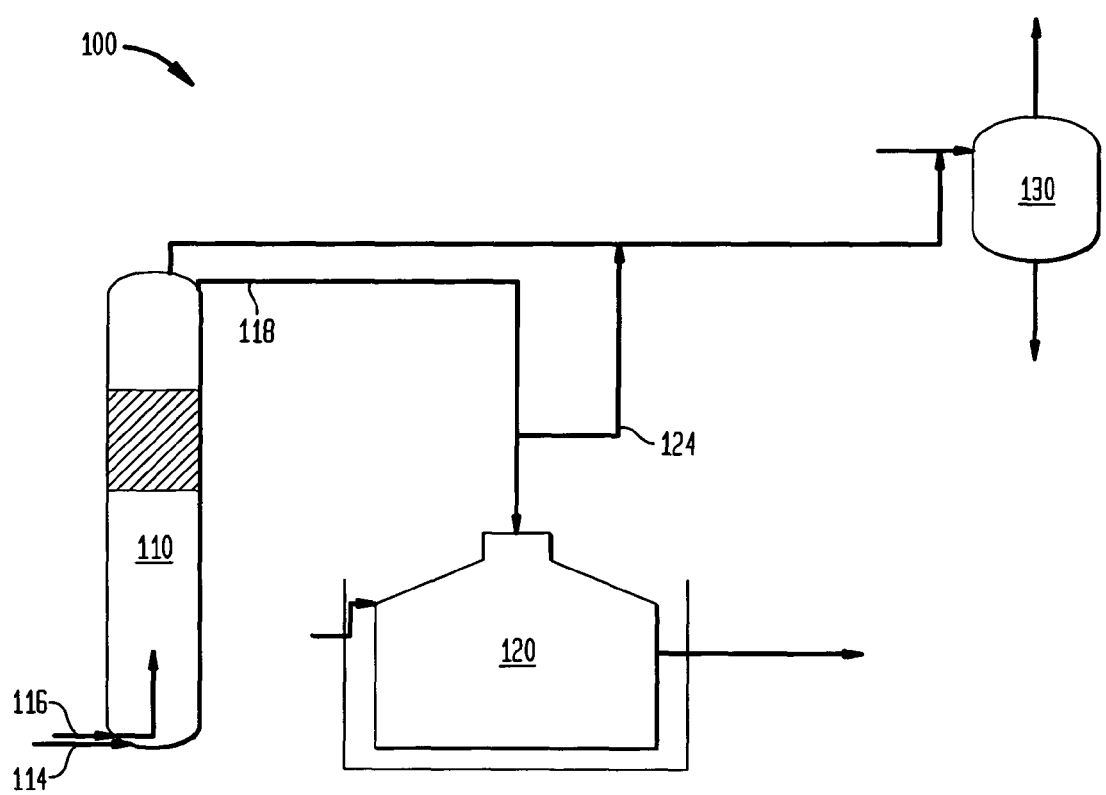
FIG. 2 is a process flow diagram illustrating one suitable industrial scale system for the production of vinyl ester from a carboxylic acid and acetylene according to this invention.

FIG. 2 illustrates one of a variety of suitable scaled-up reactor systems 100 for industrial operation. The system 100 of FIG. 2 comprises a reactor 110, a collection tank 120, and a series of knock out pots represented here by a single pot 130. The reactor 110 is charged with catalyst through the bottom of the reactor 110 and with carboxylic acid and optionally solvent via line 114. Acetylene is bubbled through the reaction medium via line 116 under a nitrogen atmosphere. The reactor is heated to a predetermined temperature and the temperature is maintained throughout a reaction time. Vinyl ester product is removed from the reactor via line 118 and collected in product collection tank 120. Gaseous substances from the reactor 110 and the collection tank 120 are routed to knock out pot 130 via line 24. The knock out pot(s) 130 serve to condense product and solvent vapors, regulate pressure, and dilute non-condensible gases.

EXAMPLES

The following examples are presented to further illustrate the present invention and should not be taken as limiting the invention, the spirit and scope of which is set forth in the appended claims. These examples are provided for illustrative purposes only and various modifications thereof can readily be made which are known to one skilled in the art.

Figure 3:
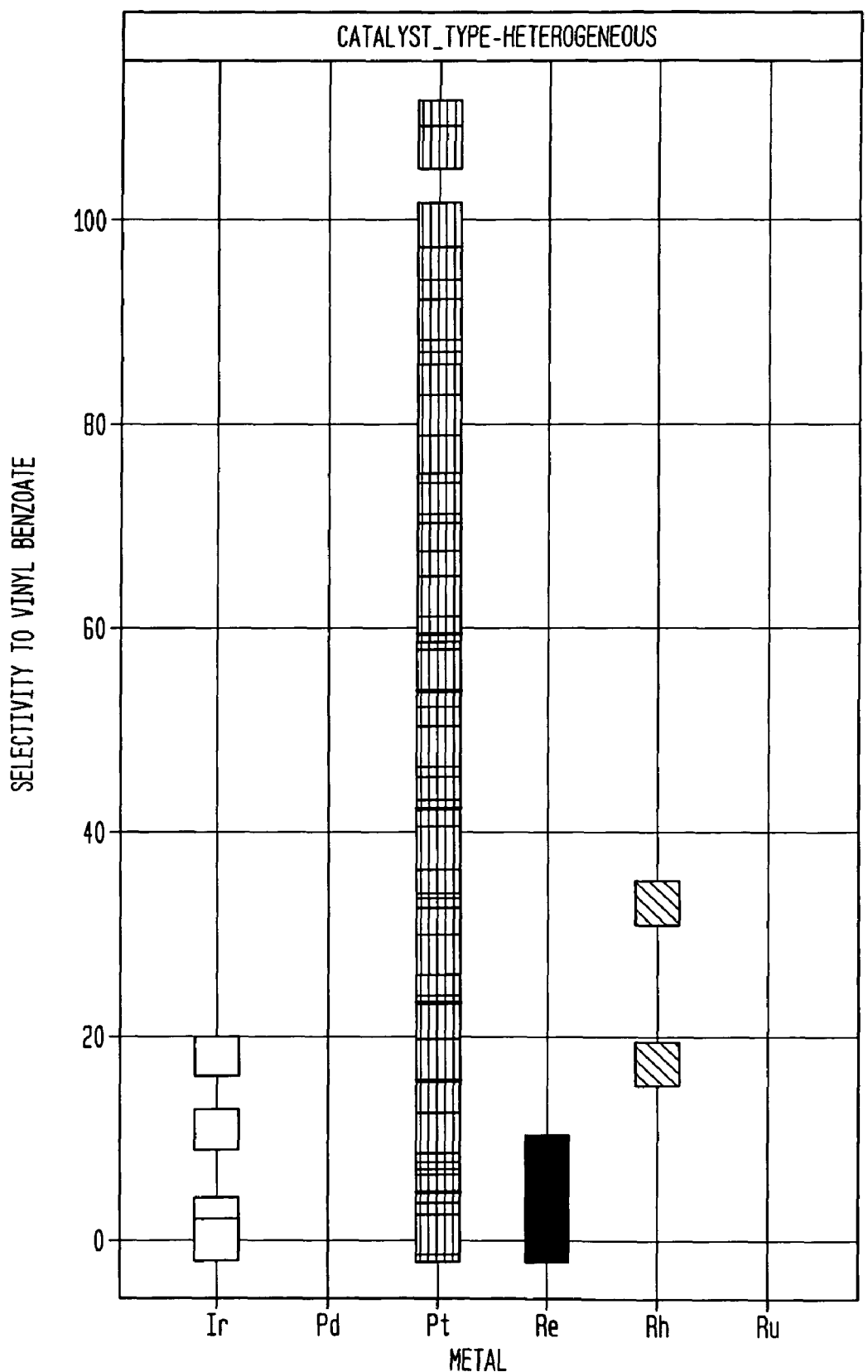
FIG. 3 is an illustration of the relative selectivity to vinyl benzoate achieved using a variety of catalyst metals according to the process of the invention.
Figure 4:
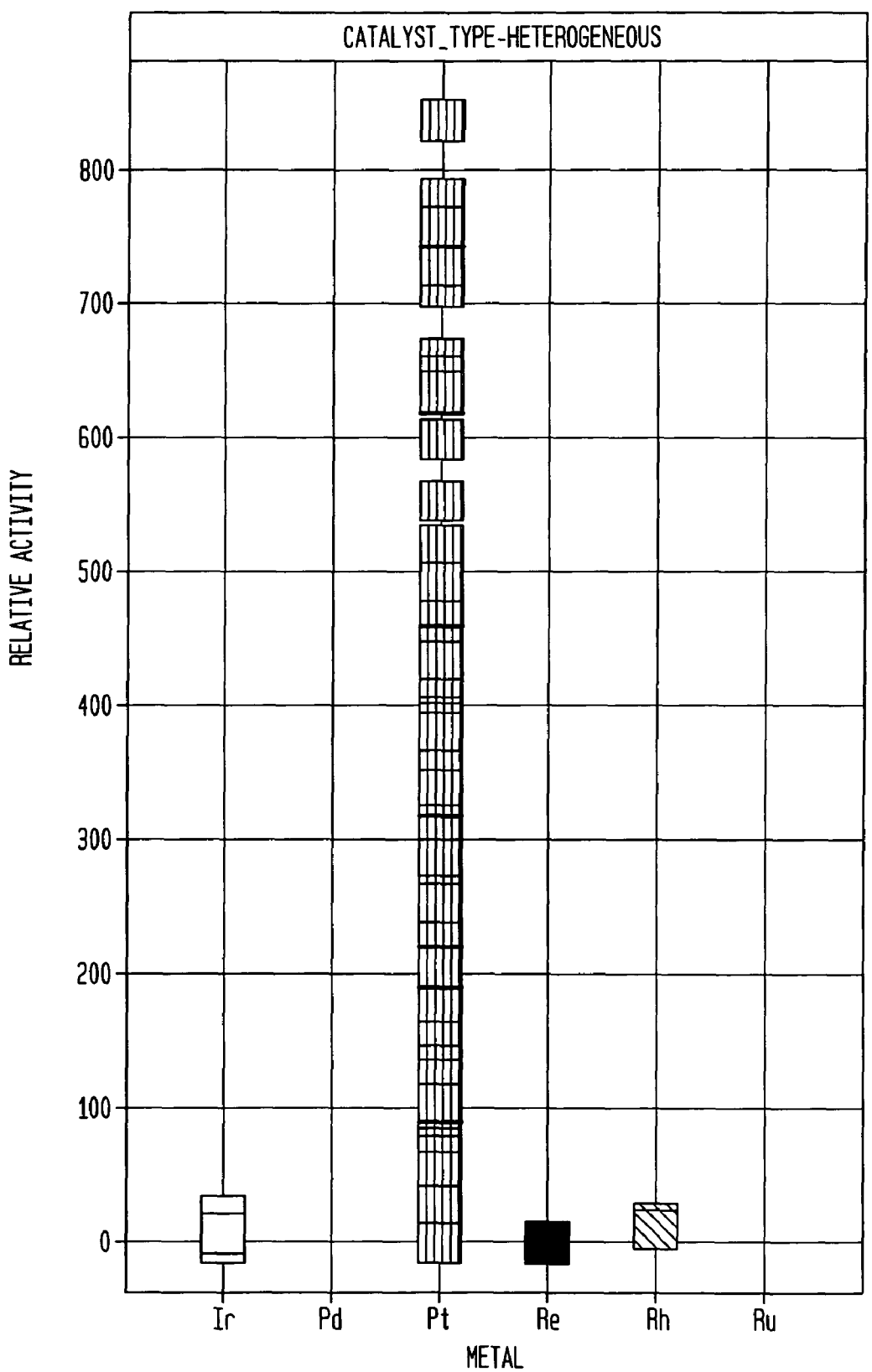
FIG. 4 is an illustration of the Relative Activity achieved using a variety of catalyst metals according to the process of the invention.

Examples 1-12 illustrate the conversion of benzoic acid to vinyl benzoate. The selectivity to vinyl benzoate and TONs achieved by Examples 1 and 3-12 are displayed in summary form in FIGS. 3 and 4, respectively. Specifically, Example 1 illustrates the process of this invention using a supported platinum metal catalyst in a batch mode.

Example 2 illustrates the process of this invention using a supported platinum catalyst in a continuous operation.

Examples 3-8 illustrate the catalytic activity of various supported platinum catalysts with or without ligands and/or additives.

Example 9 illustrates the catalytic activity of various supported rhenium metal catalysts with or without ligands and/or additives.

Example 10 illustrates the catalytic activity of various supported rhodium metal catalysts with or without ligands and/or additives.

Examples 11-12 illustrate the catalytic activity of various supported iridium metal catalysts with or without ligands and/or additives.

Examples 13-16 illustrate scale-up procedure for the conversion of benzoic acid to vinyl benzoate. Examples 17-18 illustrate the conversion of 2-ethyl hexanoic acid to vinyl 2-ethylhexanoate.

Finally, Comparative Example 1 illustrates the catalytic activity of various other supported metal catalysts for the production of vinyl benzoate under comparative reaction conditions.

As noted above, most of the supported metal catalysts are commercially available and can be used as such. The catalyst may be activated by drying in a nitrogen atmosphere at around 50-100° C. for about 16 hours. The following example describes a procedure for the preparation of various metal support catalysts employed in the process of this invention for illustrative purpose only.

Example A

Preparation of 1 Weight Percent Platinum on Carbon

Powdered and meshed carbon (99 g) of uniform particle size distribution of about 0.2 mm is dried at 120° C. in an oven under nitrogen atmosphere overnight and then cooled to room temperature. To this is added a solution of platinum nitrate (Chempur®) (1.64 g) in distilled water (16 ml). The resulting slurry is dried in an oven gradually heated to 110° C. (>2 hours, 10° C./min.). The impregnated catalyst mixture is then calcined at 500° C. (6 hours, 1° C./min). The impregnated catalyst is finally dried in an oven at 100° C. in an inert atmosphere of nitrogen for 16 hours.

Table 1 summarizes various supported metal catalysts and ligands that can be used in the process of this invention to produce vinyl benzoate (VB) selectively as described herein. Also listed are the selectivity to VB and TONs that can be attained using these catalyst systems. The Examples that follow provide more detailed results. It should be noted that similar selectivity and TONs are achieved for other vinyl esters such as vinyl 2-ethylhexanoate (V2EH) and/or vinyl neocarboxylates.

TABLE 1

Catalyst screening results within noble metal group

| Metal | Supported Metal loading level/Catalyst Support/Ligand | VB Selectivity (%) | TON |
|---|---|---|---|
| Ru | 1.85% Ruthenium/Silica/PPh$_3$ | 30 | 50 |
| Rh | 5% Rhodium/Carbon/PPh$_3$ | 65 | 80 |
| Pd | 4% Palladium/Platinum/Carbon | 20-60 | 15-25 |
|    | 3% Palladium/Platinum/Carbon | | |
| Re | 2% Rhenium/Carbon | 10 | <1 |
| Ir | 5% Iridium/Calcium Carbonate | 10-50 | 75-80 |
|    | 5% Iridium/Carbon | | |
| Pt | 0.5% Platinum/Carbon | 50-75 | 35-300 |
|    | 1% Platinum/Carbon | | |
|    | 3% Platinum/Carbon | | |
|    | 0.5% Platinum/Alumina | | |
|    | 0.9% Platinum/Zirconia | | |
|    | 5% Platinum/Titania | | |

Gas Chromatographic (GC) Analysis of the Products

The following procedure illustrates specific GC method that can be used for the conversion of benzoic acid (BA) to vinyl benzoate (VB). Similar methods can be readily set-up for other vinyl esters.

The analysis of the products was carried out by GC using a DB-FFAP 0.25 micron column (30 m×0.25 mm). A backflush column CP-Sil 5 (1 m×0.25 mm) was installed to prevent high boiling solvents being analyzed on the main column. The GC samples were generally prepared as follows. A final reaction mixture containing the reactant and product(s) (~1 mL) was diluted with toluene (4 mL) containing a precise quantity of dodecane (the internal standard). The total mixture was stirred for either 5 or 30 minutes at room temperature in order to dissolve the reactant and product(s). The 0.04 mL final sample was further diluted with toluene to ensure correct concentration ranges for the GC analysis. In some cases, the reaction mixture was diluted with 5 mL of toluene and stirred at room temperature for one hour to dissolve the reactant and product(s).

The peaks of benzoic acid and vinyl benzoate were well separated from other peaks. Dodecane was used as the external standard, which was well separated from other peaks in the chromatograph. The GC was calibrated for benzoic acid and vinyl benzoate by analyzing a set of calibration mixtures. The GC method was sensitive enough to detect 25 ppm of benzoic acid and 5 ppm of vinyl benzoate. The following temperature profile was used in this GC method: 50° C., hold time 1 minute, ramp at 20° C./min to 160° C., hold time 0 minute, ramp at 40° C./minute to 250° C., hold time 2.25 minute–the total duration of the run=11 minutes.

Example 1

A suitable reactor vessel equipped with appropriate inlets and stirring device was charged with 100 milligrams of benzoic acid and 500 ppm of para-benzoquinone. The reactor was purged two to three times with nitrogen and a constant flow of nitrogen was maintained. To this mixture was added 900 milligrams of butyl benzoate with stirring and the mixture was heated slightly if necessary to dissolve benzoic acid. To this solution was added 50 milligrams of 5% platinum supported on titania with stirring and the entire mixture was heated to 180° C. The platinum catalyst was dried at 50° C. in air for 16 hours prior to use. At this time acetylene was fed into the reactor at a steady stream maintaining the pressure of acetylene at 1.7 bars. The reaction mixture was stirred for an additional 4 hour period. At this time, a sample of the reaction mixture was removed and analyzed by GC as described above. From the GC analysis it was observed that 65 milligrams of vinyl benzoate was formed in the reaction mixture (54 percent yield), the TON was 280.

Example 2

The catalyst utilized is 5 weight percent platinum on titania, which is commercially available. The catalyst is dried at 100° C. in nitrogen for 16 hours prior to use.

In a tubular reactor made of stainless steel, having an internal diameter of 30 mm and capable of being raised to a controlled temperature, there are arranged 50 ml of 5 weight percent platinum on titania. The length of the catalyst bed after charging is approximately about 70 mm.

A feed liquid comprised essentially of a solution of 100 grams of benzoic acid in 900 grams of toluene. The reaction feed liquid is vaporized and charged to the reactor along with acetylene and nitrogen as a carrier gas with an average combined gas hourly space velocity (GHSV) of about 2500 hr$^{-1}$ at a temperature of about 200° C. and a pressure of 22 bar. A portion of the vapor effluent is passed through a gas chromatograph for analysis of the contents of the effluents.

Example 3

Example 1 was substantially repeated in several runs using the following conditions. The reaction temperature was maintained at the appropriate temperature; at least one run was operated at each of the following temperatures: 120° C., 140° C., 160° C., 170° C. and 180° C. Butyl benzoate was used as a solvent. The amount of benzoic acid used was 100 milligrams in combination with 500 ppm of para-benzoquinone and weight of the catalyst was kept similar so as to result in same metal loading level in all cases based on 50 mg of 0.5% platinum. All catalysts were dried at 50° C. in air for 16 hours prior to use. The observed results of TON and yield of VB are summarized in Table 2.

TABLE 2

| Catalyst/support | Temp. (° C.) | TON | Yield of VB (%) |
|---|---|---|---|
| 0.5% Pt/Alumina | 140 | 90 | 15 |
|  | 160 | 260 | 40 |
|  | 170 | 75 | 13 |
| 0.5% Pt/Carbon | 120 | 10 | 3 |
|  | 140 | 15 | 3 |
|  | 160 | 25-30 | 4-5 |
|  | 180 | 40-80 | 7-15 |
| 1% Pt/Carbon | 120 | 33 | 5 |
|  | 140 | 60-140 | 10-20 |
|  | 160 | 110-205 | 15-40 |
|  | 170 | 45-265 | 7-42 |
|  | 180 | 230-260 | 38-40 |
| 3% Pt/Activated Carbon | 140 | 85-100 | 14-17 |
|  | 160 | 170-180 | 25-30 |
|  | 170 | 80-140 | 15-22 |
| 5% Pt/Titania | 120 | 30 | 5 |
|  | 140 | 55-110 | 10-17 |
|  | 160 | 175-220 | 30-40 |
|  | 180 | 180-290 | 49-55 |

Example 4

Example 1 was substantially repeated in several runs using the following conditions. The reaction temperature was maintained at the appropriate temperature; at least one run was operated at each of the following temperatures: 120° C., 140° C., 160° C., 170° C. and 180° C. Butyl benzoate was used as a solvent. The amount of benzoic acid used was 230 milligrams in combination with 500 ppm of para-benzoquinone and the weight of the catalyst was kept similar so as to result in the same metal loading level in all cases based on 50 mg of 0.5% platinum. All catalysts were dried at 50° C. in air for 16 hours prior to use. The observed results of TON and yield to VB are summarized in Table 3.

TABLE 3

| Catalyst/support | Temp. (° C.) | Yield to VB (%) | TON |
|---|---|---|---|
| 0.5% Pt/Alumina | 140 | 18 | 220 |
| | 160 | 24-34 | 320-450 |
| | 170 | 10 | 130 |
| 0.5% Pt/Carbon | 120 | ~1 | 10 |
| | 140 | 1 | 15 |
| | 160 | ~3 | 35 |
| | 180 | 6.5 | 90 |
| 1% Pt/Carbon | 120 | 6.5 | 90 |
| | 140 | 3-28 | 50-420 |
| | 160 | 10-50 | 180-710 |
| | 170 | 3-4 | 30-140 |
| | 180 | 8-35 | 120-520 |
| 3% Pt/Activated Carbon | 140 | 15-17 | 140-260 |
| | 160 | 15-17 | 210-240 |
| | 170 | 4-18 | 40-230 |
| 5% Pt/Titania | 120 | 6.5 | 90 |
| | 140 | 8-22 | 120-250 |
| | 160 | 25-35 | 350-400 |
| | 180 | 4-35 | 50-520 |

Example 5

Example 1 was substantially repeated in several runs using the following conditions. The reaction temperature was maintained at the appropriate temperature; at least one run was operated at each of the following temperatures: 120° C., 140° C., 160° C., 170° C. and 180° C. Butyl benzoate was used as a solvent. The amount of benzoic acid used was 360 milligrams in combination with 500 ppm of para-benzoquinone and the weight of the catalyst was kept similar so as to result in the same metal loading level in all cases based on 50 mg of 0.5% platinum. All catalysts were dried at 50° C. in air for 16 hours prior to use. The observed results of TON, conversion and selectivity to VB are summarized in Table 4.

TABLE 4

| Catalyst/support | Temp. (° C.) | TON | Selectivity to VB (%) | Conv. (%) |
|---|---|---|---|---|
| 0.5% Pt/Alumina | 140 | 400 | 65 | 29 |
| | 170 | 450 | 50 | 39 |
| 1% Pt/Carbon | 120 | 100 | 80 | 6 |
| | 140 | 200-400 | 70-80 | 19-28 |
| | 160 | 500-790 | 40-60 | 13-55 |
| | 170 | 120-200 | 20-50 | 18-25 |
| 3% Pt/Activated Carbon | 140 | 100-300 | 75-100 | 5-18 |
| | 160 | 550 | 55 | 50 |
| | 170 | 15 | 10 | 8 |
| 5% Pt/Titania | 120 | 100 | 95 | 6 |
| | 160 | 400-520 | 60 | 37 |
| | 180 | 30-150 | 5 | 35-45 |

Example 6

Example 1 was substantially repeated in several runs using the following conditions. Three different reaction temperatures were employed: 120° C., 140° C. and 160° C. Butyl benzoate was used as a solvent. The amount of benzoic acid used was 360 milligrams in combination with 500 ppm of para-benzoquinone and the appropriate amount of supported platinum catalyst was added so as to maintain a molar BA/metal ratio of ~385. All catalysts were dried at 100° C. in nitrogen for 16 hours prior to use. Various ligands were also used with each of the supported platinum catalysts as summarized in Table 5. Also summarized in Table 5 are TON, conversion and selectivity to VB.

TABLE 5

| Pt loading level/Catalyst Support/Ligand | Temp. (° C.) | TON | Selectivity to VB (%) | Conv. (%) |
|---|---|---|---|---|
| 0.5% Pt/Alumina | 120 | 22 | 15 | 45 |
| | 140 | 25-35 | 14-15 | 45-60 |
| | 160 | 20 | 10 | 62 |
| 0.5% Pt/Alumina/1,2-DPPB | 120 | 8 | 4 | 42 |
| | 140 | 0 | 0 | 55 |
| | 160 | 10 | 4 | 58 |
| 0.5% Pt/Alumina/triphenylphosphine | 120 | 20 | 18 | 38 |
| | 140 | 10-15 | 6-11 | 40-42 |
| | 160 | 25 | 10 | 70 |
| 1% Pt/Carbon | 120 | 80 | 60 | 38 |
| | 140 | 80 | 60 | 32 |
| | 160 | 52 | 60 | 22 |
| 1% Pt/Carbon/1,2-DPPB | 120 | 26 | 45-55 | 12-14 |
| | 140 | 23 | 40 | 15 |
| | 160 | 22 | 40 | 16 |
| 1% Pt/Carbon/triphenylphosphine | 120 | 50 | 65 | 20 |
| | 140 | 58 | 65 | 22 |
| | 160 | 85 | 60 | 35 |
| 5% Pt/Titania | 120 | 45 | 80 | 15 |
| | 140 | 65 | 80 | 25 |
| | 160 | 88 | 60 | 40 |
| 5% Pt/Titania/1,2-DPPB | 120 | 0 | 0 | 0 |
| | 140 | 0 | 0 | 0 |
| | 160 | 0 | 0 | 0 |
| 5% Pt/Titania/triphenylphosphine | 120 | 10 | 55 | 5 |
| | 140 | 10-30 | 62-65 | 1-10 |
| | 160 | 30 | 60 | 12 |

Example 7

Example 1 was substantially repeated in several runs using the following conditions. The reaction temperature was maintained at 140° C. for all runs. Butyl benzoate was used as a solvent. The amount of benzoic acid used was 360 milligrams in combination with 500 ppm of para-benzoquinone. The appropriate amount of supported platinum metal catalyst was used to attain three different levels of molar BA/metal ratios of 385, 1155 and 3850. All catalysts were dried at 100° C. in nitrogen for 16 hours prior to use. Various ligands were also used with each of the supported platinum metal catalysts as summarized in Table 7 with these varied molar BA/metal ratios. Also summarized in Table 6 are TON, conversion and selectivity to VB.

TABLE 6

| Pt loading level/Catalyst Support/Ligand | BA/metal ratio | TON | Selectivity to VB (%) | Conv. (%) |
|---|---|---|---|---|
| 0.5% Pt/Alumina | 385 | 20-30 | 19 | 45-60 |
| | 1155 | 200 | 62 | 28 |
| | 3850 | 430 | 85 | 12 |
| 0.5% Pt/Alumina/1,2-DPPB | 385 | 0 | 0 | 55 |
| | 1155 | 60 | 62 | 10 |
| | 3850 | 100 | 55 | 5 |

TABLE 6-continued

| Pt loading level/Catalyst Support/Ligand | BA/metal ratio | TON | Selectivity to VB (%) | Conv. (%) |
|---|---|---|---|---|
| 0.5% Pt/Alumina/ triphenylphosphine | 385 | 0-20 | 3-10 | 40 |
|  | 1155 | 180 | 55 | 28 |
|  | 3850 | 210 | 100 | 5 |
| 1% Pt/Carbon | 385 | 70 | 60 | 33 |
|  | 1155 | 160 | 100 | 13 |
|  | 3850 | 380 | 100 | 8 |
| 1% Pt/Carbon/1,2-DPPB | 385 | 30 | — | — |
|  | 1155 | 60 | — | — |
|  | 3850 | 100 | — | — |
| 1% Pt/Carbon/ triphenylphosphine | 385 | 60 | 62 | 23 |
|  | 1155 | 180 | 85 | 18 |
|  | 3850 | 250 | 100 | 5 |
| 5% Pt/Titania | 385 | 60 | 75-80 | 25 |
|  | 1155 | 200 | 98 | 19 |
|  | 3850 | 200 | 100 | 5 |
| 5% Pt/Titania/1,2-DPPB | 385 | 10 | — | — |
|  | 1155 | 5 | — | — |
|  | 3850 | 20 | — | — |
| 5% Pt/Titania/ triphenylphosphine | 385 | 5-30 | — | — |
|  | 1155 | 80 | — | — |
|  | 3850 | 70 | — | — |

Example 8

Example 1 was substantially repeated in several runs using the following conditions. Two different reaction temperatures were employed: 140° C. and 160° C. The selected temperature was maintained throughout the reaction. Butyl benzoate was used as a solvent. The amount of benzoic acid used was 100 milligrams in combination with 500 ppm of para-benzoquinone and the appropriate amount of supported platinum catalyst required to maintain a consistent metal loading level equivalent to 50 mg of 0.5% platinum on carbon. All catalysts were dried at 100° C. in nitrogen for 16 hours prior to use. Various ligands and additives were also used with a few of the supported platinum catalysts as summarized in Table 7. Also summarized in Table 7 are the conversion and selectivity to VB.

TABLE 7

| Pt loading level/Catalyst Support/Ligand or additive | Temp. (° C.) | Selectivity to VB (%) | Conv. (%) |
|---|---|---|---|
| 1% Pt/Carbon | 140 | 99 | 14 |
|  | 180 | 4 | 77 |
| 3% Pt/activated carbon | 140 | 98 | 4 |
|  | 160 | 66 | 68 |
| 5% Pt/titania | 140 | 96 | 18 |
|  | 180 | 62 | 86 |
| 1% Pt/carbon/1,2-DPPB | 140 | 93 | 3 |
| 0.5% Pt/alumina | 160 | 90 | 17 |
| 5% Pt/titania (mineral oil as solvent in this run) | 140 | 90 | 19 |
| 1% Pt/carbon/PPh$_3$ | 140 | 85 | 17 |
| 1% Pt/carbon/sodium benzoate | 160 | 82 | 23 |
| 5% Pt/titania/benzoic anhydride | 160 | 76 | 61 |
| 0.5% Pt/carbon | 140 | 75 | 1.7 |
|  | 160 | 2 | 68 |
| 5% Pt/activated carbon | 160 | 62 | 42 |
| 5% Pt/alumina | 160 | 60 | 51 |
| 5% Pt/carbon | 160 | 59 | 45 |
| 10% Pt/carbon | 160 | 58 | 39 |
| 5% Pt/alumina-silica powder | 160 | 54 | 30 |
| 1% Pt/carbon/ tetrabutylammonium acetate | 160 | 45 | 37 |
| 5% Pt/Barium sulfate | 160 | 37 | 13 |
| 1% Pt/carbon/tributylamine | 160 | 36 | 41 |
| 1% Pt/graphite | 160 | 26 | 9 |
| 5% Pt/calcium carbonate | 160 | 21 | 12 |
| 0.04% Pt/pentasil(zeolite)-alumina | 160 | 22 | 36 |
| 0.9% Pt/zirconia | 160 | 64 | 70 |
| 5% Pt/silica | 160 | 20 | 11 |
| 0.5% Pt/alumina/1,2-DPPB | 140 | 62 | 9 |
| 5% Pt/titania/PPh$_3$ | 140 | 63 | 11 |

Example 9

Example 1 was substantially repeated except for using the following conditions. The amount of catalyst was 50 milligrams of two weight percent rhenium supported on carbon and the reaction was run at 140 or 160° C. Butyl benzoate was used as a solvent. The amount of benzoic acid used was 100 milligrams in combination with 500 ppm of para-benzoquinone. The conversion of benzoic acid at 140° C. was 4% and the selectivity to VB was 3%, and at 160° C. the conversion of benzoic acid was 3% and the selectivity to VB was 8%. An additional run was performed at 140° C. using mineral oil as a solvent. The conversion of benzoic acid was 2% and the selectivity to VB was 2%. Finally, a run was performed using rhenium(VII) sulfide at 120° C. using butyl benzoate as a solvent. The conversion of benzoic acid was 8% and the selectivity to VB was less than 1%.

Example 10

Example 1 was substantially repeated in two runs except for using the following conditions. The amount of catalyst used was 50 milligrams of five weight percent rhodium supported on carbon with and without triphenylphosphine and the reaction was run at 160° C. Butyl benzoate was used as a solvent. The amount of benzoic acid used was 360 mg in combination with 500 ppm of para-benzoquinone. The conversion of benzoic acid and the selectivity to VB are summarized in Table 8.

TABLE 8

| Rh loading level/Catalyst Support/Ligand | Temp. (° C.) | Selectivity to VB (%) | Conv. (%) |
|---|---|---|---|
| 5% Rh/Carbon | 160 | 33 | 11 |
| 5% Rh/Carbon/PPh$_3$ | 160 | 18 | 16 |

Example 111

Example 1 was substantially repeated in several runs using the following conditions. In all runs the reaction temperature was maintained at 160° C. Butyl benzoate was used as a solvent. The amount of benzoic acid used was 100 mg, 200 mg and 360 mg in combination with 500 ppm of para-benzoquinone. Fifty milligrams (with 100 or 200 mg of benzoic acid) or 29.44 mg (with 360 mg of benzoic acid) of five weight percent iridium metal, supported either on calcium carbonate or carbon, was used. This resulted in molar BA/metal ratio of 67, 126 and 385 respectively for 100, 200 and 360 mg benzoic acid charged into the reactor. The TON, conversion and selectivity to VB obtained in these runs are summarized in Table 9.

TABLE 9

| Ir loading level/Catalyst Support | Amt. of BA | TON | Selectivity to VB (%) | Conv. (%) |
|---|---|---|---|---|
| 5% Ir/Calcium carbonate | 100 | 15 & 23 | 45 & 50 | 48 & 80 |
| | 200 | 37 | 33 | 90 |
| | 360 | 21 | 18 | 29 |
| 5% Ir/Carbon | 100 | 9 | 40 | 35 |
| | 360 | 5 | 11 | 11 |

Example 12

Example 1 was substantially repeated in three runs except for using 50 milligrams of iridium supported on a catalyst support and the reaction was run at 160° C. Butyl benzoate was used as a solvent. The amount of benzoic acid used was 100 milligrams in combination with 500 ppm of para-benzoquinone. The conversion of benzoic acid and the selectivity to VB are summarized in Table 10.

TABLE 10

| Ir loading level/Catalyst Support | Temp. (° C.) | Selectivity to VB (%) | Conv. (%) |
|---|---|---|---|
| 5% Ir/Calcium carbonate | 160 | 18 | 29 |
| 5% Ir/Carbon | 160 | 11 | 12 |
| Ir(IV) oxide | 160 | 2 | 13 |

Example 13

A suitable reactor vessel of the class shown in FIG. 2 was equipped with appropriate inlets and stirring device and was charged with 50.08 grams of benzoic acid and 2 grams of methylhydroquinone. The reactor was purged two to three times with nitrogen and a constant flow of nitrogen was maintained. To this mixture was added 133 grams of butyl benzoate with stirring and the mixture was heated slightly, if necessary, to dissolve benzoic acid. To this solution was added 1 gram of 5% platinum supported on carbon with stirring and the entire mixture was heated to 180° C. At this time acetylene was fed into the reactor at a steady stream and at a rate of 100 mL/min. The reaction mixture was stirred for an additional 4 hour period. At this time, a sample of the reaction mixture was removed and analyzed by GC as described above. From the GC analysis it was observed that 25.37 grams of vinyl benzoate was formed in the reaction mixture (42 percent yield). 21 grams of unreacted benzoic acid were recovered; Conversion of BA=59%; Selectivity to VB=71%; and the TON was 670.

Example 14

A suitable reactor vessel of the class shown in FIG. 2 was equipped with appropriate inlets and stirring device was charged with 18.05 grams of benzoic acid and 2 grams of methylhydroquinone. The reactor was purged two to three times with nitrogen and a constant flow of nitrogen was maintained. To this mixture was added 159 grams of butyl benzoate with stirring and the mixture was heated slightly, if necessary, to dissolve benzoic acid. To this solution was added 2.67 grams of 2% platinum supported on alumina with stirring and the entire mixture was heated to 200° C. At this time acetylene was fed into the reactor at a steady stream and at a rate of 100 mL/min. The reaction mixture was stirred for an additional 4 hour period. At this time, a sample of the reaction mixture was removed and analyzed by GC as described above. From the GC analysis it was observed that 5.37 grams of vinyl benzoate was formed in the reaction mixture (25 percent yield). 12.93 grams of unreacted benzoic acid were recovered; Conversion of BA=28%; Selectivity to VB=87%; and the TON was 130.

Example 15

A suitable reactor vessel of the class shown in FIG. 2 was equipped with appropriate inlets and stirring device and was charged with 18.14 grams of benzoic acid and 2 grams of methylhydroquinone. The reactor was purged two to three times with nitrogen and a constant flow of nitrogen was maintained. To this mixture was added 172 grams of butyl benzoate with stirring and the mixture was heated slightly, if necessary, to dissolve benzoic acid. To this solution was added 1.65 grams of 2% platinum supported on carbon with stirring and the entire mixture was heated to 180° C. At this time acetylene was fed into the reactor at a steady stream and at a rate of 100 mL/min. The reaction mixture was stirred for an additional 2 hour period. At this time, a sample of the reaction mixture was removed and analyzed by GC as described above. From the GC analysis it was observed that 4.7 grams of vinyl benzoate was formed in the reaction mixture (21 percent yield). 13.6 grams of unreacted benzoic acid were recovered; Conversion of BA=25%; Selectivity to VB=85%; and the TON was 190.

Example 16

A suitable reactor vessel of the class shown in FIG. 2 was equipped with appropriate inlets and stirring device and was charged with 10.06 grams of benzoic acid and 2 grams of methylhydroquinone. The reactor was purged two to three times with nitrogen and a constant flow of nitrogen was maintained. To this mixture was added 172 grams of butyl benzoate with stirring and the mixture was heated slightly, if necessary, to dissolve benzoic acid. To this solution was added 1.65 grams of 2% platinum supported on carbon with stirring and the entire mixture was heated to 200° C. Acetylene was then fed into the reactor at a steady stream and at a rate of 100 mL/min. The reaction mixture was stirred for an additional 2 hours. At this time, a sample of the reaction mixture was removed and analyzed by GC as described above. From the GC analysis it was observed that 13.4 grams of vinyl benzoate was formed in the reaction mixture (32 percent yield). Conversion of BA=51%; Selectivity to VB=92%; and the TON was 370.

Example 17

A suitable reactor vessel of the class shown in FIG. 1 was equipped with appropriate inlets and stirring device and was charged with 49.74 grams of 2-ethylhexanoic acid, 136.3 grams of butyl benzoate and 2 grams of methylhydroquinone. The reactor was purged two to three times with nitrogen and a constant flow of nitrogen was maintained. To this mixture was added 0.99 grams of 5% platinum supported on carbon with stirring and the entire mixture heated to 180° C. Acetylene was then fed into the reactor at a steady stream and at a rate of 100 mL/min. The reaction mixture was stirred for an additional 4 hours. At this time, a sample of the reaction mixture was removed and analyzed by GC as described above. From the GC analysis it was observed that 9.9 grams of vinyl 2-ethylhexanoate was formed in the reaction mixture (17 percent yield). 33 grams of unreacted 2-ethylhexanoic acid were recovered; Selectivity to V2EH=42%; and the TON was 240.

Example 18

A suitable reactor vessel of the class shown in FIG. 1 was equipped with appropriate inlets and stirring device and was charged with 40.34 grams of 2-ethylhexanoic acid, 136.3 grams of butyl benzoate and 2 grams of methylhydroquinone. The reactor was purged two to three times with nitrogen and a constant flow of nitrogen was maintained. To this mixture was added 0.99 grams of 5% platinum supported on carbon with stirring and the entire mixture was heated to 200° C. At this time acetylene was fed into the reactor at a steady stream and at a rate of 100 mL/min. The reaction mixture was stirred for an additional 4 hour period. At this time, a sample of the reaction mixture was removed and analyzed by GC as described above. From the GC analysis it was observed that 19.4 grams of vinyl 2-ethylhexanoate was formed in the reaction mixture (41 percent yield). Conversion of 2-EHA=33%; Selectivity to V2EH=58%; and the TON was 450.

Comparative Example 1

Example 1 was substantially repeated in several runs except for using various one or more metals supported on a catalyst support. The metals tested were aluminum, bismuth, cerium, cobalt, chromium, iron, molybdenum, nickel, lead, antimony, scandium, tin, vanadium, tungsten, and zirconium as a single metal supported on carbon. Also included in this comparative study was a catalyst comprising a combination of metals of lanthanum, cerium, cobalt, and copper supported on carbon. Another catalyst tested contained a combination of yttrium, barium and copper supported on carbon. The reactions were run at a temperature range of 50° C. to 180° C. depending upon the type of catalysts used as follows:
- 50° C. and 10 mg of: Co, Cr, Mo, Ni and W supported catalysts;
- 80° C. and 10 mg of: Co, Cr, Mo, Ni and W supported catalysts;
- 120° C. and 50 mg of: Co, Cr, Mo, Ni and W supported catalysts;
- 160° C. and 50 mg of LaCeCoCu, Ni and YBaCu supported catalysts;
- 180° C. and 50 mg of: Al, Bi, Ce, Co, Cr, Fe, Mo, Ni, Pb, Sb, Sc, Sn, V and Zr supported catalysts.

In all runs butyl benzoate was used as the solvent. In all runs the amount of benzoic acid used was 100 milligrams in combination with 500 ppm of para-benzoquinone and 10 or 50 milligrams of the catalyst as noted above. The results showed that TONs were below 0.1 for most of the catalysts in this group, and none of the TONs exceeded 20.

While the invention has been described in connection with several embodiments, modifications of those embodiments within the spirit and scope of the present invention will be readily apparent to those of skill in the art. The invention is defined in the appended claims.

What is claimed is:

1. A heterogeneous process for selective formation of a vinyl ester from a carboxylic acid comprising: reacting a carboxylic acid, optionally dissolved in a suitable organic solvent, with acetylene in the presence of a supported platinum catalyst at a suitable reaction temperature and pressure, wherein the platinum loading of the catalyst is from about 0.1 weight % up to about 10 weight % and the support is selected from carbon, activated carbon, titania, alumina, or zirconia, wherein the carboxylic acid is selected from the group consisting of 2-ethylhexanoic acid, benzoic acid, neopentanoic acid, neoheptanoic acid, neodecanoic acid, propionic acid, butyric acid, valeric acid, heptanoic acid, acrylic acid, methacrylic acid, and stearic acid.

2. The process according to claim 1, wherein said carboxylic acid is benzoic acid.

3. The process according to claim 1, wherein said carboxylic acid is 2-ethylhexanoic acid.

4. The process according to claim 1, wherein the reaction temperature ranges from about 50° C. to about 180° C.

5. A heterogeneous process for the selective formation of a vinyl ester from a carboxylic acid which comprises reacting the carboxylic acid with acetylene at a suitable reaction temperature and pressure in the presence of a supported platinum catalyst without ligand, wherein the carboxylic acid is selected from the group consisting of 2-ethylhexanoic acid, benzoic acid, neopentanoic acid, neoheptanoic acid, neodecanoic acid, propionic acid, butyric acid, valeric acid, heptanoic acid, acrylic acid, methacrylic acid, and stearic acid.

6. The process according to claim 5, wherein the catalyst support is carbon, activated carbon, or titania.

7. The process according to claim 5, wherein the reaction temperature ranges from about 100° C. to about 180° C.

8. The process according to claim 5, wherein the reaction temperature ranges from about 140° C. to about 200° C.

9. The process according to claim 1, wherein the support is carbon or activated carbon and wherein the platinum is present at a loading level of from about 0.5 weight percent to about 6 weight percent.

10. The process according to claim 1, wherein the process is further characterized by a selectivity to the vinyl ester of at least 50%.

11. The process according to claim 1, wherein the process is further characterized by a carboxylic acid conversion of at least 50%.

12. The process according to claim 5, wherein the pressure is from about 1 atmosphere absolute to about 2 atmospheres absolute.

13. A heterogeneous process for the selective formation of a vinyl ester from a carboxylic acid which comprises reacting the carboxylic acid with acetylene, optionally in a suitable organic solvent, at a suitable pressure and temperature, in the presence of a supported metal catalyst, wherein the catalyst metal is selected from the group consisting of iridium, platinum, and rhodium, and is supported on an inorganic support selected from the group consisting of carbon, activated carbon, graphite, silica, titania, alumina, calcium silicate, calcium carbonate, silica-alumina, silica aluminate, zirconia, barium carbonate, and barium sulfate, wherein the carboxylic acid is selected from the group consisting of 2-ethylhexanoic acid, benzoic acid, neopentanoic acid, neoheptanoic acid, neodecanoic acid, propionic acid, butyric acid, valeric acid, heptanoic acid, acrylic acid, methacrylic acid, and stearic acid.

14. The process according to claim 13, wherein the process further comprises the presence of one or more ligands selected from the group consisting of triphenylphosphine and 1,2-diphenylphosphinobenzene (1,2-DPPB).

15. The process according to claim 13, wherein the process further comprises the presence of one or more additives selected from the group consisting of potassium acetate, lithium chloride, sodium benzoate, sodium chloride, sodium iodide, benzoic anhydride, tri-(n-butyl)amine, tetra-(n-butyl) ammonium chloride and tetrabutylammonium acetate.

16. The process according to claim 13, wherein the carboxylic acid is dissolved in a suitable organic solvent selected from the group consisting of acetonitrile, benzonitrile, butyl benzoate, mineral oil, diethylene glycol dibutylether and toluene.

* * * * *